(12) United States Patent
Kroemer et al.

(10) Patent No.: US 9,938,528 B2
(45) Date of Patent: Apr. 10, 2018

(54) METHODS AND PHARMACEUTICAL COMPOSITIONS FOR TREATING HUMAN IMMUNODEFICIENCY VIRUS TYPE 1 (HIV-1) INFECTIONS

(71) Applicants: INSERM (Institut National de la Sante et de la Recherche Medicale), Paris (FR); Universite Paris-Sud, Orsay (FR); Institut Gustave Roussy, Villejuif (FR); Universite Paris Descartes, Paris (FR); Universite Pierre et Marie Curie (Paris 6), Paris (FR); Institut Pasteur, Paris (FR); Istituto Nazionale per Le Malattie Infettive IRCCS Lazzaro Spallanzani, Rome (IT); Assistance Publique-Hopitaux de Paris (APHP), Paris (FR)

(72) Inventors: Guido Kroemer, Paris (FR); Jean-Luc Perfettini, Villejuif (FR); Marie-Lise Gougeon, Paris (FR); Awatef Allouch, Villejuif (FR); Mauro Piacentini, Rome (IT)

(73) Assignees: INSTITUT NATIONAL DE LA SANTE ET DE LA RECHERCHE MEDICALE (INSERM), Paris (FR); UNIVERSITE PARIS-SUD, Orsay (FR); INSTITUT GUSTAVE ROUSSY, Villejuif (FR); UNIVERSITE PARIS DECARTES, Paris (FR); UNIVERSITE PIERRE ET MARIE CURIE, Paris (FR); INSTITUT PASTEUR, Paris (FR); INSTITUTO NAZIONALE PER LE MALATTIE INFETTIE IRCCS LAZZARO SPALLANZANI, Rome (IT); ASSISTANCE PUBLIQUE HOPITAUX DE PARIS (APHP), Paris (FR)

( * ) Notice: Subject to any disclaimer, the term of this patent is extended or adjusted under 35 U.S.C. 154(b) by 0 days.

(21) Appl. No.: 15/534,321

(22) PCT Filed: Dec. 10, 2015

(86) PCT No.: PCT/EP2015/079310
§ 371 (c)(1),
(2) Date: Jun. 8, 2017

(87) PCT Pub. No.: WO2016/092041
PCT Pub. Date: Jun. 16, 2016

(65) Prior Publication Data
US 2017/0342411 A1    Nov. 30, 2017

(30) Foreign Application Priority Data

Dec. 11, 2014   (EP) ................................ 14307001

(51) Int. Cl.
| | |
|---|---|
| *C12N 15/11* | (2006.01) |
| *C12N 15/113* | (2010.01) |
| *A61K 45/06* | (2006.01) |
| *A61K 31/683* | (2006.01) |
| *A61K 31/5517* | (2006.01) |
| *A61K 31/165* | (2006.01) |
| *A61K 31/395* | (2006.01) |
| *A61K 31/17* | (2006.01) |
| *A61K 31/713* | (2006.01) |
| *C12Q 1/18* | (2006.01) |

(52) U.S. Cl.
CPC .......... *C12N 15/113* (2013.01); *A61K 31/165* (2013.01); *A61K 31/17* (2013.01); *A61K 31/395* (2013.01); *A61K 31/5517* (2013.01); *A61K 31/683* (2013.01); *A61K 31/713* (2013.01); *A61K 45/06* (2013.01); *C12Q 1/18* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 2007/0161559 A1* | 7/2007 | Petrilli ................ | C07K 16/245 514/220 |
| 2010/0048675 A1 | 2/2010 | Bagasra | |

FOREIGN PATENT DOCUMENTS

| | | |
|---|---|---|
| EP | 0 713 705 A1 | 5/1996 |
| WO | 2013/134030 A1 | 9/2013 |

OTHER PUBLICATIONS

Zhou et al.; "Genome-Scale RNAi Screen for Host Factors Required for HIV Replication"; Cell Host & Microbe, vol. 4, No. 5, Nov. 1, 2008, pp. 495-504.

* cited by examiner

*Primary Examiner* — Ekaterina Poliakova-Georgantas
(74) *Attorney, Agent, or Firm* — Whitham, Curtis & Cook

(57) ABSTRACT

The present invention provides methods and pharmaceutical compositions for treating human immunodeficiency virus type 1 (HIV-1) infections. In particular, the present invention relates to a method for treating HIV-1 infection in a subject in need thereof comprising administering the subject with a therapeutically effective amount of an inhibitor of SGT1 activity or expression.

19 Claims, 14 Drawing Sheets

Figure 1A:
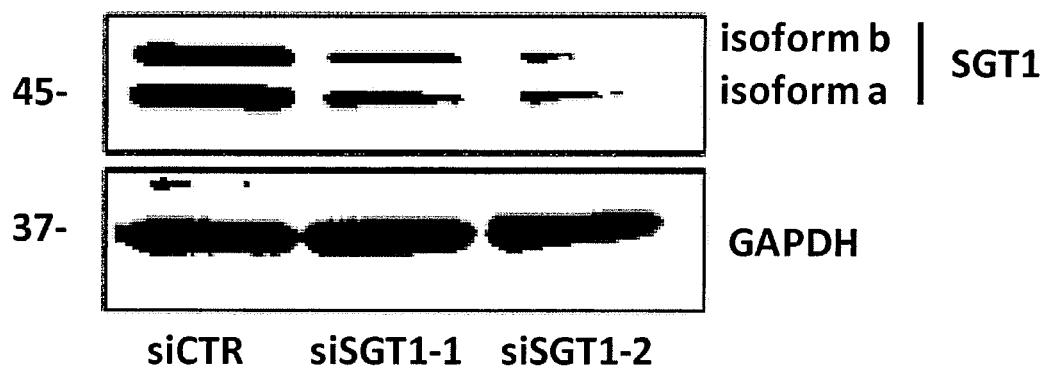

METHODS AND PHARMACEUTICAL COMPOSITIONS FOR TREATING HUMAN IMMUNODEFICIENCY VIRUS TYPE 1 (HIV-1) INFECTIONS

FIELD OF THE INVENTION

The present invention provides methods and pharmaceutical compositions for treating human immunodeficiency virus type 1 (HIV-1) infections.

BACKGROUND OF THE INVENTION

HIV-1 infection poses a public health problem that is partially controlled by a combination of specific antiretroviral agents that targets viral proteins. Nonetheless, the surge of multi-resistant HIV-1 strains will require the development of novel antiviral strategies. The search of new anti-retroviral compounds that affect viral-cellular interfaces represents a new challenge to provide new therapies that could alternate HAART therapy and reduce the emergence of HIV-1 resistant strains. During all the steps of HIV-1 replication in the main target cells (activated CD4 T cells and macrophages) the virus takes advantages of the functions of cellular proteins to accomplish its infection or to hide its replication from the immune system response [1-4].

Numerous cellular proteins that promote HIV-1 infection have been identified either by wide throughout screening or by single studies that decipher the role of each factor in viral entry, uncoating, reverse transcription, nuclear import, integration, transcription, viral RNA export and translation, assembly and budding [5-8]. Host proteins have been involved in the virological synapse formation and in the cell-to-cell-transmission of HIV-1, which is the most efficient mode of viral dissemination [9, 10]. Nevertheless, most of the identified HIV-1 cellular co-factors have been discovered using epithelial cell based in vitro systems that do not express endogenously HIV-1 receptor (CD4) and co-receptors (CCR5 and CXCR4), and do not have the same biology of macrophages and activated CD4 T cells. The use of CD4$^+$ T cell lines and monocytic cell lines improved the field in validating the role of the identified cellular proteins in HIV-1 replication. However, the big issues remain the validation of the roles of these cellular factors on in vitro differentiated primary macrophages or activated CD4 T cells and during in vivo (acute and chronic) HIV-1 infections.

The identification of molecular mechanisms by which HIV-1 uses the host proteins to accomplish efficiently its replication is required for the design of novel drugs that are able to target specifically viral-cellular interfaces and inhibit the infection. This strategy will—with no doubt—avoid the emergence of viral resistance strains after anti-retroviral therapies using drugs that target directly the HIV-1 proteins. For example, LEDGIN peptides abolish the protein-protein interaction between LEDGF/p75 and HIV-1 integrase. These peptides strongly inhibit HIV-1 replication by avoiding the tethering of HIV-1 pre-integration complex to the chromatin of host genome by LEDGF/p75 and by reducing the viral integrase catalytic activity [11].

SUMMARY OF THE INVENTION

The present invention provides methods and pharmaceutical compositions for treating human immunodeficiency virus type 1 (HIV-1) infections. In particular, the present invention is defined by the claims.

DETAILED DESCRIPTION OF THE INVENTION

The inventors identified the ubiquin ligase associated protein SGT1 as a new cellular factor that promotes strongly early steps of HIV-1 replication in primary macrophages and activated T lymphocytes and should be a potential target for HIV-1 therapy.

Accordingly, the present invention relates to a method for treating HIV-1 infection in a subject in need thereof comprising administering the subject with a therapeutically effective amount of an inhibitor of SGT1 activity or expression.

The method of the invention is carried out with any subject. The subject is in particular a mammal, more particularly a primate and more preferably still, a human. Subjects may be male or female and may be of any age, including prenatal (i.e., in utero), neonatal, infant, juvenile, adolescent, adult, and geriatric subjects. Thus, in some cases the subjects may be pregnant female subjects. In some embodiments, the method is carried out with a subject at risk of developing a HIV-1 infection.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken. The terms "prophylaxis" or "prophylactic use" and "prophylactic treatment" as used herein, refer to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. In some embodiments, the method of the present invention relates to a prophylactic treatment.

The method of the present invention is particularly suitable for preventing HIV-1 transmission. The method of the present invention is also particularly suitable for eradicating the bulk of viral load from the majority of cells (in particular T CD4 cells and macrophages) following HAART (Highly Active Antiretroviral Therapy). The method of the present invention is also particularly suitable for purging and eradicating the HIV-1 virus from the subject (i.e. latent HIV reservoir). The method of the present invention is also particularly suitable for purging and eradicating resistant HIV-1 strains (i.e. HIV-1 strains that are resistant to HAART). The method of the present invention is also expected to reduce the likelihood of spread of HIV infection to new subjects.

As used herein the term "SGT1" has its general meaning in the art and refers to SUGT1 SGT1, suppressor of G2 allele of SKP1. The human gene is homologous to the yeast gene SGT1, which encodes a protein involved in kinetochore function and required for the G1/S and G2/M transitions. Complementation studies suggest that the human protein has similar functions. Two transcript variants encoding different isoforms have been found for this gene (SEQ ID NO:1 and SEQ ID NO:2).

(SGT1A)

SEQ ID NO: 1
MAAAAGTAT SQRFFQSFSD ALIDEDPQAA LEELTKALEQ

KPDDAQYYCQ RAYCHILLGN YCVAVADAKK SLELNPNNST

-continued

```
AMLRKGICEY HEKNYAAALE TFTEGQKLDS ADANFSVWIK

RCQEAQNGSE SEVWTHQSKI KYDWYQTESQ VVITLMIKNV

QKNDVNVEFS EKELSALVKL PSGEDYNLKL ELLHPIIPEQ

STFKVLSTKI EIKLKKPEAV RWEKLEGQGD VPTPKQFVAD

VKNLYPSSSP YTRNWDKLVG EIKEEEKNEK LEGDAALNRL

FQQIYSDGSD EVKRAMNKSF MESGGTVLST NWSDVGKRKV

EINPPDDMEW KKY (SGT1B)
                                    SEQ ID NO: 2
MAAAAAGTAT SQRFFQSFSD ALIDEDPQAA LEELTKALEQ

KPDDAQYYCQ RAYCHILLGN YCVAVADAKK SLELNPNNST

AMLRKGICEY HEKNYAAALE TFTEGQKLDI ETGFHRVGQA

GLQLLTSSDP PALDSQSAGI TGADANFSVW IKRCQEAQNG

SESEVWTHQS KIKYDWYQTE SQVVITLMIK NVQKNDVNVE

FSEKELSALV KLPSGEDYNL KLELLHPIIP EQSTFKVLST

KIEIKLKKPE AVRWEKLEGQ GDVPTPKQFV ADVKNLYPSS

SPYTRNWDKL VGEIKEEEKN EKLEGDAALN RLFQQIYSDG

SDEVKRAMNK SFMESGGTVL STNWSDVGKR KVEINPPDDM

EWKKY
```

In some embodiments, the inhibitor according to the invention may be a low molecular weight antagonist, e.g. a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In some embodiments, the inhibitor according to the invention is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Then after raising aptamers directed against the SGT1 as above described, the skilled man in the art can easily select those blocking the said receptor or channel.

In another embodiment, the inhibitor according to the invention is an inhibitor of gene expression. An "inhibitor of gene expression" refers to a natural or synthetic compound that has a biological effect to inhibit or significantly reduce the expression of a gene.

Inhibitors of gene expression for use in the present invention may be based on anti-sense oligonucleotide constructs. Anti-sense oligonucleotides, including anti-sense RNA molecules and anti-sense DNA molecules, would act to directly block the translation of the mRNA by binding thereto and thus preventing protein translation or increasing mRNA degradation, thus decreasing the level of the protein (e.g. SGT1), and thus activity, in a cell. For example, antisense oligonucleotides of at least about 15 bases and complementary to unique regions of the mRNA transcript sequence encoding the targeted protein (e.g. SGT1) can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of gene expression for use in the present invention. Gene expression can be reduced by contacting a subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and in particular cells expressing the targeted proteins (e.g. SGT1). In particular, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Typical viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

By a "therapeutically effective amount" is meant a sufficient amount of the inhibitor to treat an HIV-1 infection at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The inhibitor according to the invention is typically combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The active ingredient can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In some embodiments, the inhibitor according to the invention is used in combination with other active ingredients, such as antivirals (e.g. HAART), antibiotics, immunomodulators or vaccines. Antiretroviral typically include nucleoside/nucleotide reverse transcriptase inhibitors (such as abacavir, emtricitabine, and tenofovir) nonnucleoside reverse transcriptase inhibitors (NNRTIs), such as efavirenz, etravirine, and nevirapine; protease inhibitors (PIs), such as atazanavir, darunavir, and ritonavir; entry inhibitors, such as enfuvirtide and maraviroc; integrase inhibitors, such as dolutegravir and raltegravir. Example of antiviral include but are not limited to pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; nonnucleoside reverse transcriptase inhibitors such as nevirapine (11-cyclopropyl-5,11-dihydro-4-methyl-6H-dipyrido-[3,2-b:2',3'-e][1,4]diazepin-6-one), efavirenz, delavirdine, and the like; phosphonate reverse transcriptase inhibitors, e.g. tenofovir and the like; compounds of the TIBO (tetrahydro-imidazo[4,5,1-jk][1,4]-benzodiazepine-2 (1H)-one and thione)-type e.g. (S)-8-chloro-4,5,6,7-tetrahydro-5-methyl-6-(3-methyl-2-butenyl)imidazo-[4,5,1-jk] [1,4]benzo-diazepine-2(1H)-thione; compounds of the [alpha]-APA ([alpha]-anilino phenyl acetamide) type e.g. [alpha]-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; ribonucleotide reductase inhibitors, e.g. hydroxyurea and the like. Combinations may as well exert a synergistic effect in inhibiting HIV-1 replication when components of the combination act on different or same sites of HIV-1 replication, in particular on different sites. The use of such combinations may reduce the dosage of a given conventional antiretroviral agent which would be required for a desired prophylactic effect as compared to when that agent is administered as a single active ingredient. These combinations reduce potential of resistance to single agent, while minimizing any associated toxicity. These combinations may also increase the efficacy of the conventional agent without increasing the associated toxicity.

In a further aspect, the present invention relates to an inhibitor of SGT1 activity or expression for use in the treatment of HIV-1 infection in a subject in need thereof.

A further object of the invention relates to a method for screening a drug for the treatment of an HIV-1 infection comprising the steps of i) providing a candidate compound ii) determining whether the candidate compound is an inhibitor of SGT1 activity or expression and iii) positively selecting the candidate compound which is an inhibitor of SGT1 activity or expression.

According to one embodiment of the invention, the candidate compound may be selected from a library of compounds previously synthesised, or a library of compounds for which the structure is determined in a database, or from a library of compounds that have been synthesised de novo or natural compounds. The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. No. 5,475,096 and U.S. Pat. No. 5,270,163.

The candidate compounds that have been positively selected at the end the in vitro screening which has been described previously may be subjected to further selection steps in view of further assaying its anti-HIV-1 biological properties. For this purpose, the candidate compounds that have been positively selected with the general in vitro screening method as above described may be further selected for their ability to inhibit HIV-1 viral entry.

In some embodiments of the method above, step ii) of said screening method comprises the following steps: (1) infecting cultured mammalian cells with HIV-1 virus (e.g. NL4.3 X4 HIV-1 virus); (2) bringing into contact the infected cells obtained at steps (1) with a candidate compound that has been positively selected; (3) determining the HIV-1 replication; and (4) comparing the HIV-1 replication determined at step (3) with the HIV-1 infectivity that is determined when step (2) is performed in the absence of the said positively selected compound. In some alternative embodiments, step (2) is performed before step (1).

According to the method as above described, step (1) may be performed either prior to or after step (2) depending of the embodiment under consideration. For performing step (1), mammalian cells encompass primary culture cells as well as cell lines. Primary culture cells include primary cultures from mammalian peripheral blood mononuclear cells (PBMC), primary cultures from mammalian blood lymphocytes and primary cultures from mammalian monocytes or mammalian macrophages. In some embodiments, primary culture cells are pre-activated before their use in step (1) of the above described method. Mammalian cells also encompass mammalian cells originating from various mammalian cell lines, in particular, mammalian cell lines expressing CD4 receptors at their membrane surface. Preferred mammalian cells consist of human cells. Cell lines typically include but are not limited to HeLa CD4 or MT4 or Jurkat or CEMss or any mammalian cell lines expressing CD4. In some embodiments, it may be suitable to perform a first screening test on the cell lines and perform a second screening test on the primary cells (which may be a precious and rare material that shall be used with parsimony). Thus illustratively, step (1) may be performed by infecting HeLa cells expression CD4 receptor, for example by cell transfection with the well known HIV HXB2R molecular clone. Step (2) as above described may be performed by adding an amount of the candidate compound to be tested to the culture medium wherein the (i) already HIV infected or (ii) the not yet HIV infected cells are cultured. Usually, a plurality of culture samples are prepared, so as to add increasing amounts of the candidate compound to be tested in distinct culture samples. Generally, at least one culture sample without candidate compound is also prepared as a negative control for further comparison. Optionally, at least one culture sample with an already known inhibitor of the SGT1 is also prepared as a positive control for standardisation of the method. Step (3) as above described may be performed by any well known method in the art. As described in the EXAMPLE, the efficiency of HIV-1 infection can be determined by measuring the release of p24CA in the supernatant of macrophages infected during 72 hours. Therefore, step (4) may be performed by comparing the HIV-1 infection data obtained for the cell cultures incubated with the candidate compound to be tested with the HIV-1 infection data obtained for the negative control cell cultures without the said candidate compound nor the known inhibitor of the SGT1. Illustratively, the efficiency of the candidate compound may be assessed by comparing (i) the HIV-1 infection measured in the cell cultures that were incubated therewith with (ii) the HIV-1 infection measured in the cell cultures that were incubated with the known inhibitor of the SGT1. Further illustratively, the efficiency of the candidate compound may be assessed by determining for which amount of the candidate compound added to the cell cultures the HIV-1 infection is close to the amount of HIV-1 infection found for the known inhibitor of the SGT1.

The invention will be further illustrated by the following figures and examples. However, these examples and figures should not be interpreted in any way as limiting the scope of the present invention.

FIGURES

FIG. 1: SGT1 silencing inhibits HIV-1 replication without affecting CD4 and CXCR4 expressions in HeLa CD4+ CXCR4+. HeLa CD4$^+$CXCR4$^+$LTR-Lac-Z$^+$ cells were silenced (si-SGT1-1 and si-SGT1-2) or not (siRNA-CTR) for SGT1 with two different siRNAs. (A) At 48 hours post-siRNA transfection: SGT1 silencing was verified by Western blot analysis. (B) At 48 hours post-siRNA transfection: silenced cells were infected with NL4.3 X4 HIV-1 at MOI 1. Infections were determined at 24 hours post-infection by measuring the beta-galactosidase activity with respect to control cells (siCTR). (C) Cytotoxicity effects of siSGT1-1 and siSGT1-2 siRNAs were controled by the MTT assay with respect to control siRNA (siCTR) at 48 hours and 96 hours post-siRNA transfection. (D) At 72 hours post infection, HIV-1 productions were determined by quantifying CAp24 by ELISA from the cell supernatant of SGT1 silenced cells (siSGT1-1) and control cells (siCTL). The expressions of CD4 and CXCR4 receptors on the membrane of HeLa CD4+CXCR4+LTR-Lac-Z+ cells silenced (siSGT1-1) or not (siCTR) for SGT1 were controlled by Flow cytometry analysis of life cells at 48 hours post siRNA transfections for the percentage (E) and the mean fluorescence intensity (MFI) (F).

FIG. 2: SGT1 silencing inhibits HIV-1 replication in primary Monocytes Derived Macrophages (MDM). MDM from three different healthy donors (EFS7, EFS10 and EFS17) were transfected with smart pool siRNAs targeting SGT1 gene (siSGT1). Control MDM were transfected with a pool of non-targeting siRNAs (siCTL). (A-C top panels) At 96 hours post-siRNA transfection SGT1 silencing in MDM of different donors was verified by Western blot analysis. (A-C middle panels). At 96 hours post-siRNAs transfection: silenced MDM were infected with AD8 HIV-1 R5 virus (10 ng p24 for $1\times10^6$ MDM). At 72 hours post infections, HIV-1 productions were determined by quantifying CAp24 by ELISA from the cell supernatant of SGT1 silenced MDM (siSGT1) and control cells (siCTL). The data are means±SD of triplicate wells. (A-C bottom panels) Cytotoxicity effects of SGT1 silencing mediated by siSGT-1 siRNAs transfections comparing to control cells were controlled by the WST-1 cell proliferation assay at 96 hours post-siRNAs transfections. The data are means±SD of triplicate wells.

FIG. 3: SGT1 silencing inhibits HIV-1 replication in activated CD4 T cells. Activated CD4 T cells from two healthy donors (EFS13 and EFS20) were transfected with smart pool siRNAs targeting SGT1 gene (siSGT1). Control cells were transfected with a pool of non-targeting siRNAs (siCTL). (A and B top panels) At 72 hours post-siRNA transfection SGT1 silencing in T lymphocytes was verified by Western blot analysis. (A and B middle panels) At 72 hours post-siRNAs transfection: silenced activated CD4 were infected with NL4.3 HIV-1 X4 virus (100 ng p24 for $1\times10^6$ CD4 T cells). At 72 hours post infections, HIV-1 productions were determined by quantifying CAp24 by ELISA from the cell supernatant of SGT1 silenced lymphocytes (siSGT1) and control cells (siCTL). The data are means±SD of triplicate wells. (A bottom panel) Cytotoxicity effects of SGT1 silencing mediated by siSGT-1 siRNAs transfections comparing to control cells (siCTL) were controlled by the WST-1 cell proliferation assay at 72 hours post-siRNAs transfections. The data are means±SD of triplicate wells. (B bottom panel) Cytotoxicity effects of SGT1 silencing mediated by siSGT-1 siRNAs transfections comparing to control cells (siCTL) were controlled by measuring the lactate dehydrogenase activity in the supernatant of cells at 72 hours post-siRNAs transfections. The data are means±SD of triplicate wells.

FIG. 4: SGT1 silencing inhibits reverse transcription and nuclear import. (A and B) MDM from two different healthy donors (EFS10 and EFS17) and activated T cells from two donors (EFS13 and EFS20) were transfected with smart pool siRNAs targeting SGT1 gene (siSGT1). Control cells were transfected with a pool of non-targeting siRNAs (siCTL). MDM and activated T cells were infected at 96 hours and 72 hours, respectively, post-silencing with NL4.3 delta Env-Luc (VSV-G) HIV-1 strain (10 ng p24 for $1\times10^6$ MDM and 100 ng p24 $1\times10^6$ activated T cells). Viral infectivity was determined by Luciferase activity at 72 hours post-infection. The data are means±SD of triplicate wells. In FIGS. 3 and 4 the same donors were infected in parallel with replication competent R5 or X4 viruses. (C, D, E and F) MDM from two different healthy donors (EFS27 and EFS29) and activated T cells from one donor (EFS30) were transfected with smart pool siRNAs targeting SGT1 gene (siSGT1). Control cells were transfected with a pool of non-targeting siRNAs (siCTL). MDM and activated T cells were infected at 96 hours and 72 hours post-silencing, respectively, with NL4.3 delta Env-Luc (VSV-G) HIV-1 strain pre-treated with Dnase I (10 ng p24 for $1\times10^6$ MDM and 100 ng p24 for $1\times10^6$ activated T cells). MDM and activated T cells were harvest at 24 hours and 6 hours post-infection, respectively, to analyze HIV-1 early reverse transcripts by qPCR. At 72 hours and 24 hours post-infection, MDM and activated T cells were harvest, respectively, to analyze HIV-1 Late Reverse Transcripts by qPCR. For HIV-1 two-LTRs circles analysis by qPCR, MDM and activated T cells were harvest at 72 hours and 24 hours, respectively. The integrated HIV-1 proviruses were determined by Alu-nested qPCR at 72 hours and 24 hours post-infection of MDM and activated CD4 T cells, respectively. The primers, probes and experimental procedure of HIV-1 DNA qPCR were previously described in Allouch et al-2013-PNAS and David et al-2006-journal of Immunology.

EXAMPLE

Figure 1B:
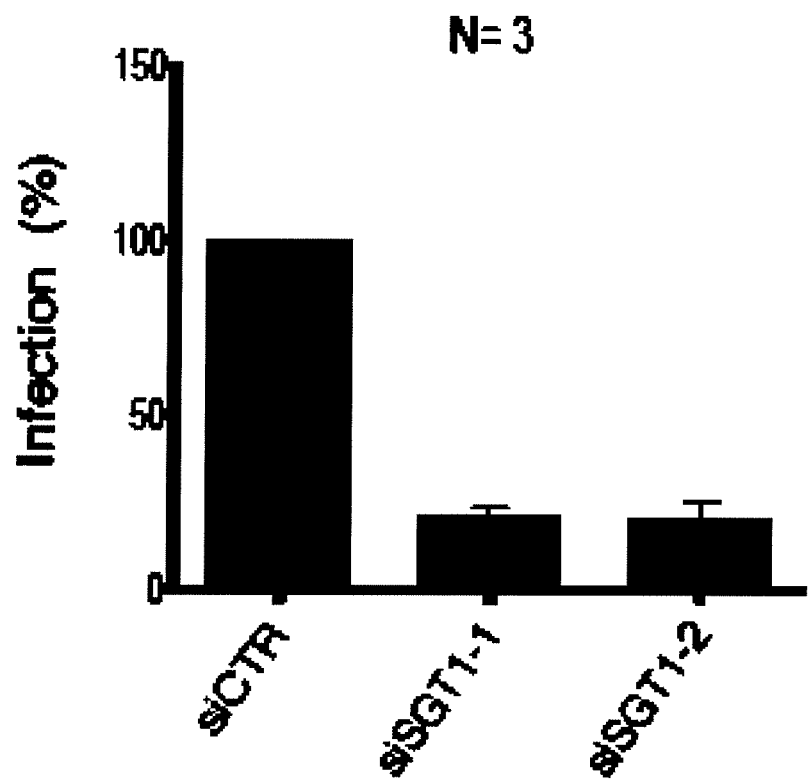
Figure 1C:
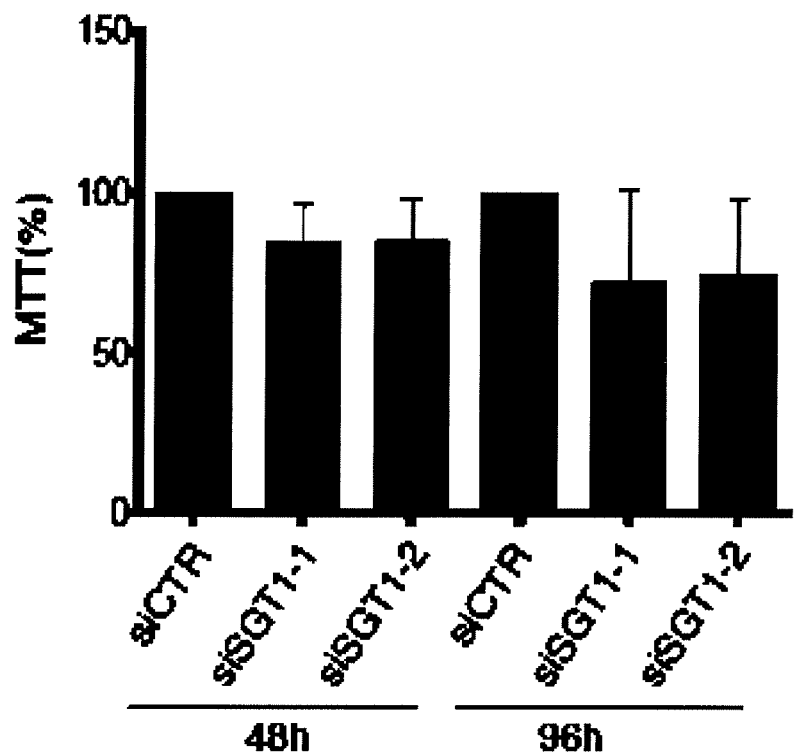

The protein SGT1 is an indispensable cellular factor for HIV-1 replication. In order to identify new proteins involved in the early steps of HIV-1 replication we characterized the role of SGT1 which is a protein that was described to have a role in the innate immune response in plants and in mammals [12, 13]. Indeed, SGT1 (suppressor of G2 allele of skp1) was described to be a co-chaperone of Heat Shock protein 90 (HSP90) and plays a role in the stabilization, maturation and activation of NLR proteins [14-16]. NLR (nucleotide binding domain and leucine-rich repeat containing) proteins provide pathogen-sensing systems that are conserved in plants and in animals [14, 16]. They can be activated directly or indirectly by pathogen derived molecules and cellular stress [14, 17]. Although SGT1 is highly conserved in eukaryotes [18], its precise role remains unclear as it controls a number of unrelated processes ranging from yeast/human kinetochore assembly [18, 19] to the activation of ubiquitin ligases [18], adenylyl cyclase and polo kinases [20]. To explore the role of SGT1 in HIV-1 infection, SGT1 was silenced with two different small interfering RNA (siSGT1-1 and siSGT1-2) that efficiently reduce expression of both SGT1 isoforms in HeLa cell lines that express stably the chemokine receptor CD4 and co-receptor CXCR4 and a LacZ gene under the HIV-1 LTR promoter (HeLa CD4+CXCR4+LTR-LacZ+)(FIG. 1A). Then HeLa CD4+CXCR4+LTR-LacZ+ cells were infected with the $NL_{4.3}$ (X4) envelope (Env) HIV-1 replication competent virus. The HIV-1 infectivity was determined at 24 hours post-infection by measuring the β-galactosidase activity from LTR-LacZ reporter gene that is activated by viral Tat protein from the HIV-1 viral particles that infect cells. Importantly, HIV-1 infectivity was significantly reduced in three independent experiments, by 80 to 90% in the cells silenced with the two different SGT1 siRNAs (siSGT1-1 and siSGT1-2) comparing to control cells transfected with control siRNA (siCTR) (FIG. 1B). In these experiments, cell viability was controlled by measuring cytotoxicity (using MTT test) and we did not detect any cytotoxic effect of SGT1 silenced cells with respect to control cells (FIG. 1C) indicating that SGT1 silencing affected directly HIV-1 infectivity.

Figure 1D:
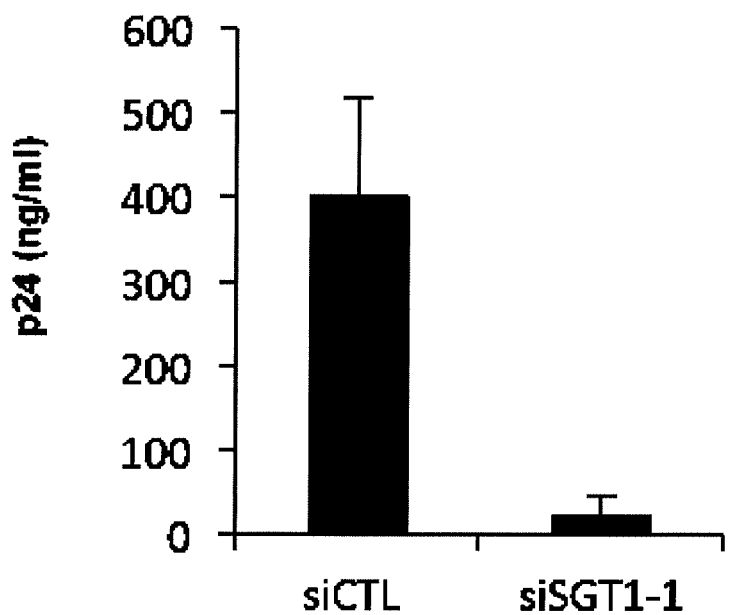
Figure 1E:
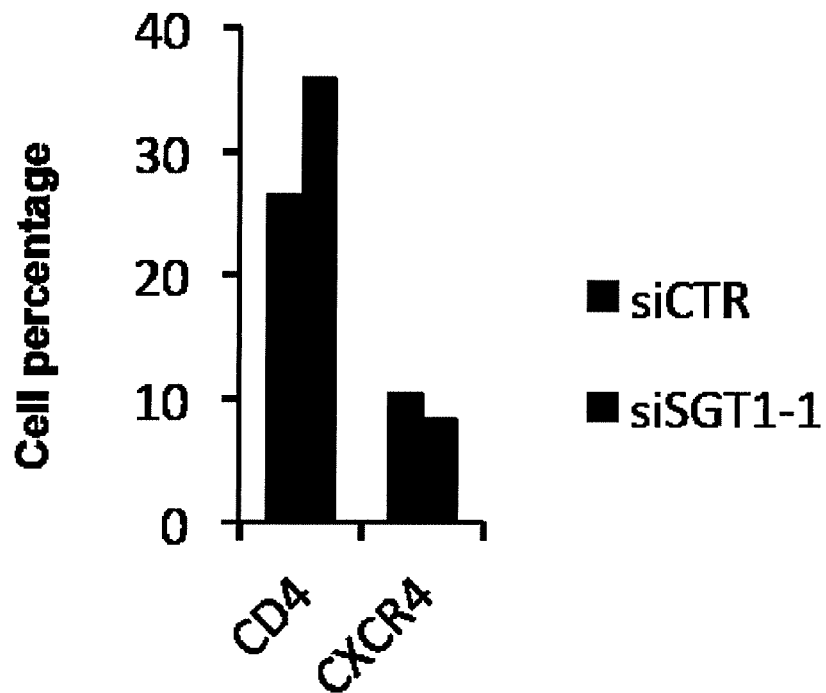
Figure 1F:
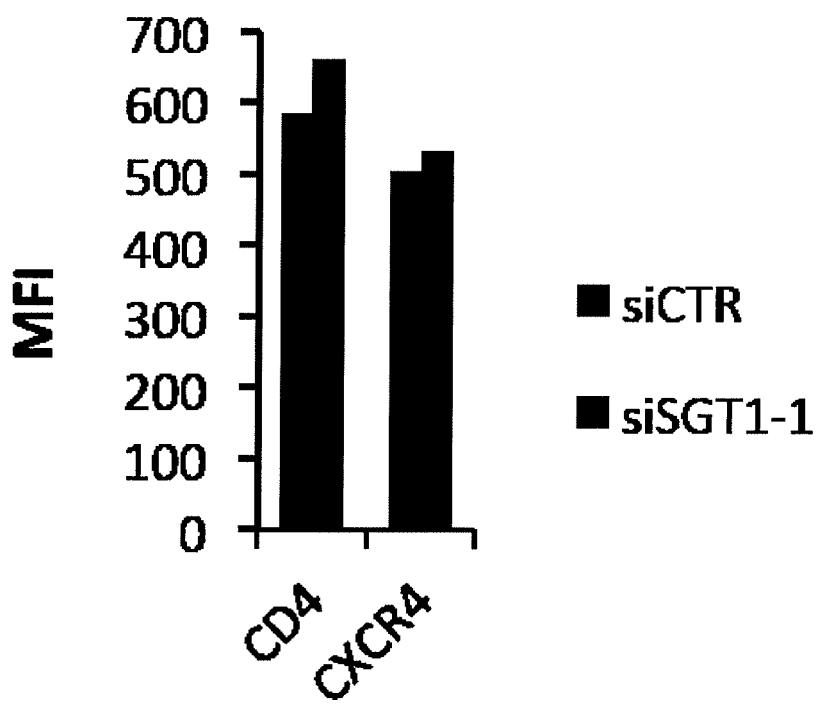
Figure 2A:
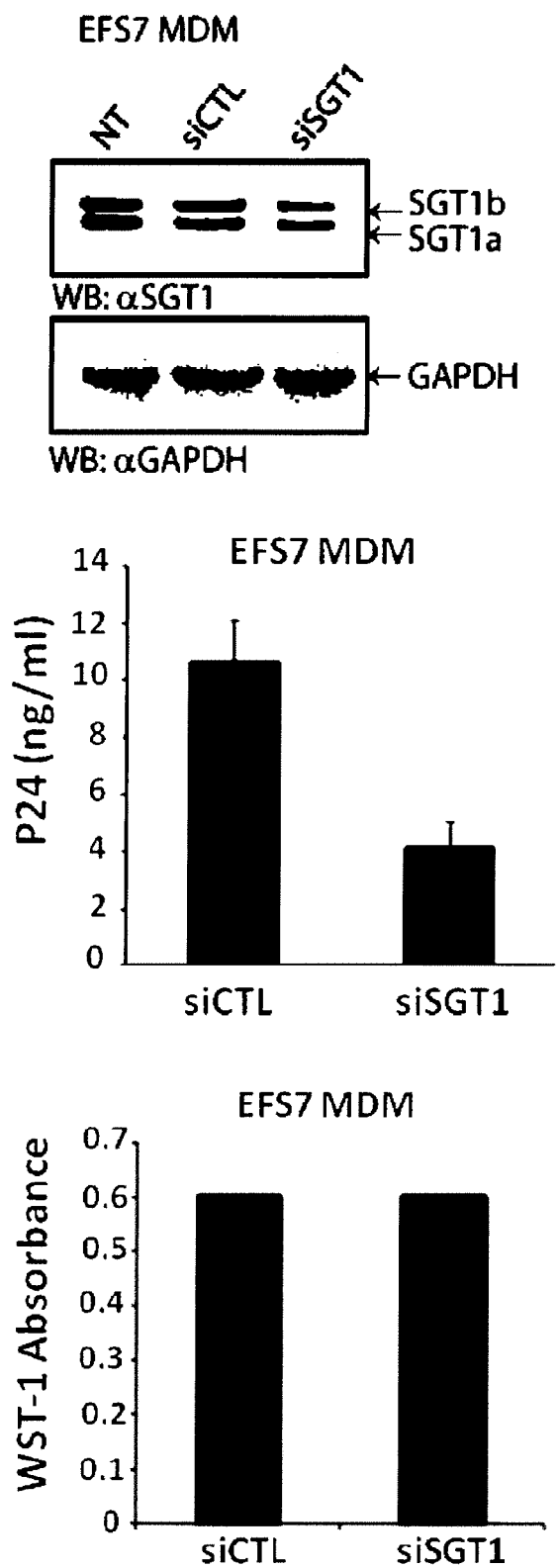
Figure 2B:
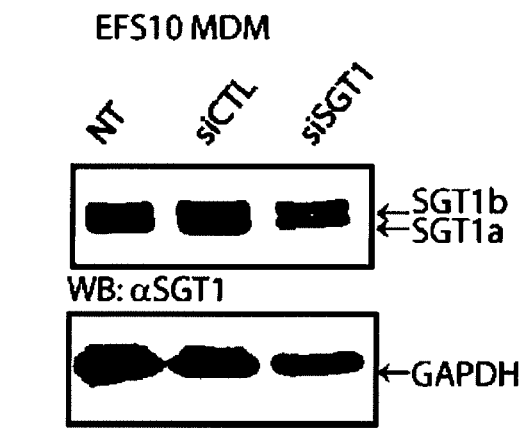
Figure 2B:
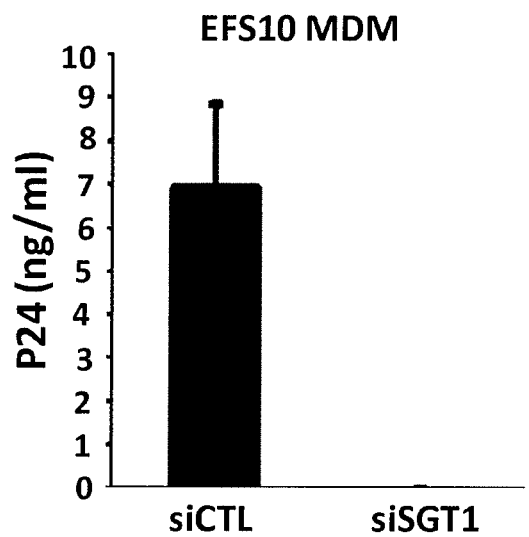
Figure 2B:
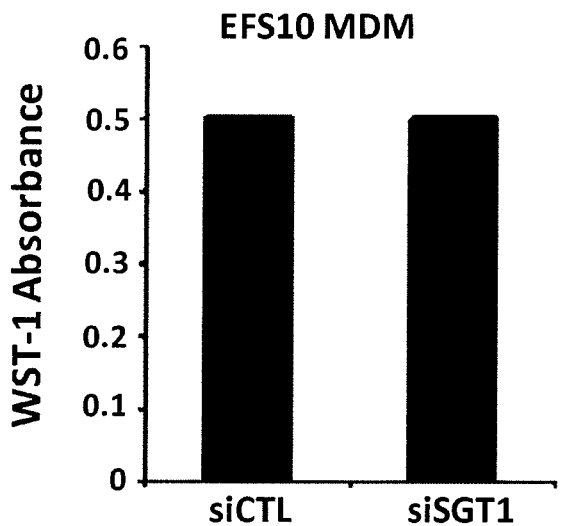
Figure 2C:
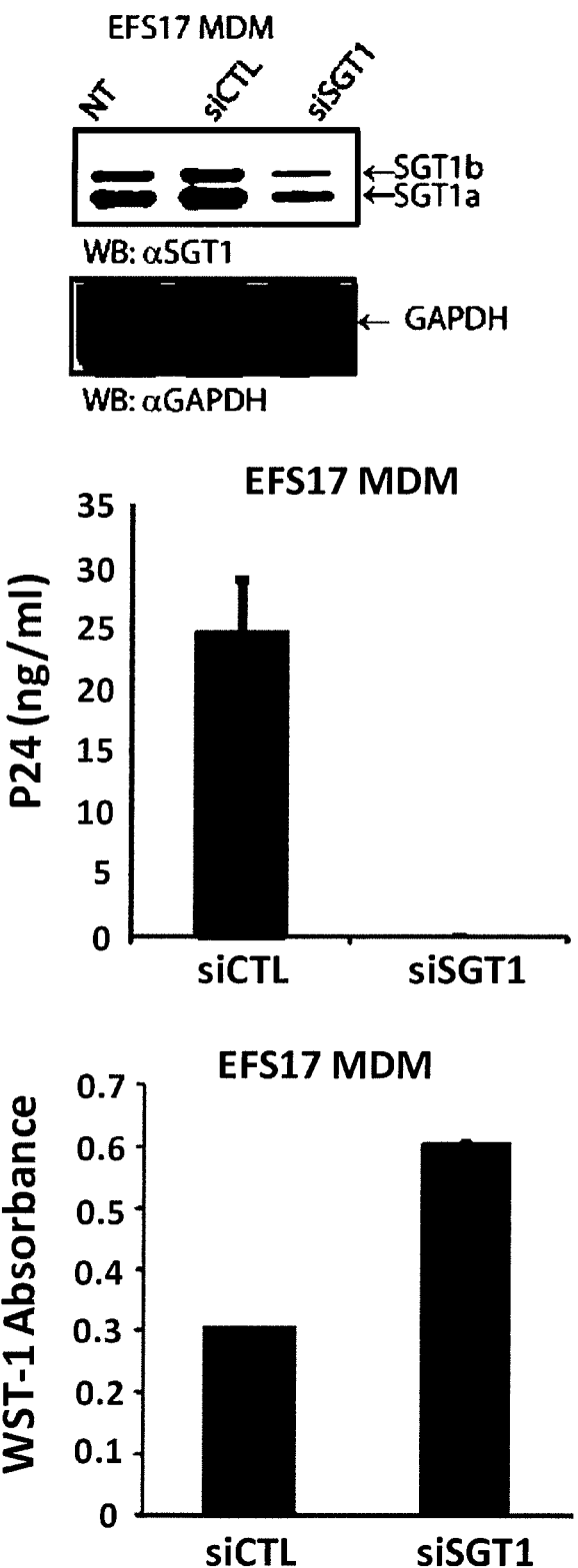

The replication of NL$_{4.3}$ (X4) Env HIV-1 virus in SGT1 silenced HeLa cells was also determined by the quantification of the produced HIV-1 in the supernatant of cells at 72 hours post-infection by the HIV-1 CAp24 ELISA. Results reported in FIG. 1D showed that NL4.3 HIV-1 production, as quantified for CAp24 antigen content, was reduced by 94% in the supernatant of SGT1 silenced cells (siSGT1-1) comparing to control cells (siCTR) further demonstrating that the depletion of SGT1 abrogates HIV-1 replication. In order to understand whether SGT1 knockdown affects the expressions of CD4 and CXCR4 chemokine receptors on the cell surface of CD4$^+$CXCR4$^+$LTR-LacZ$^+$ cells, we analyzed by Flow cytometry the percentage of cells expressing both receptors and the intensity of their expressions following SGT1 knockdown at 48 hours post siRNA transfection. No significant differences were found neither in the percentage of cells expressing CD4 and CXCR4 (FIG. 1E) nor in the receptors expressions intensities (FIG. 1F) following the silencing of SGT1. This result indicates that the depletion of SGT1 inhibits HIV-1 replication without affecting expressions of CD4 and CXCR4 receptors. All the above data strongly suggest that SGT1 is a crucial factor for HIV-1 replication.

We then validated the role of SGT1 during HIV-1 infection of primary cells targets of HIV-1 (macrophages and activated CD4 T cells). Monocyte Derived Macrophages (MDM) were differentiated from Peripheral Blood Mononuclear Cells (PBMCs) obtained from buffy coats of different healthy donors of Etablissement Français du Sang (EFS). Macrophages were silenced for SGT1 through the transfection of smart pool siRNAs containing four different siRNAs targeting SGT1 gene (siSGT1). Control cells were transfected with a pool of non-targeting siRNAs (siCTL). After 96 hours of transfection, macrophages were infected with AD8 HIV-1 viral strain (that has R5 type Env).

Figure 3A:
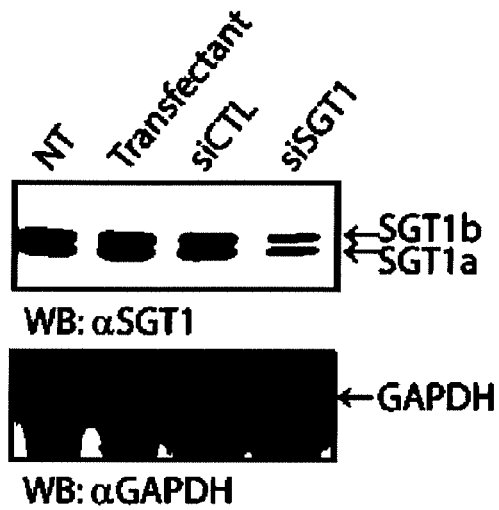
Figure 3A:
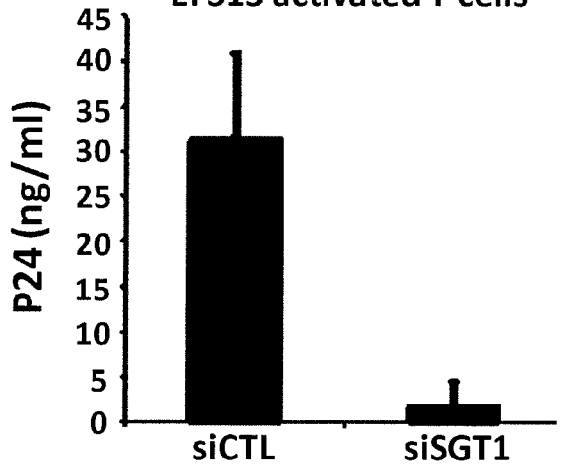
Figure 3A:
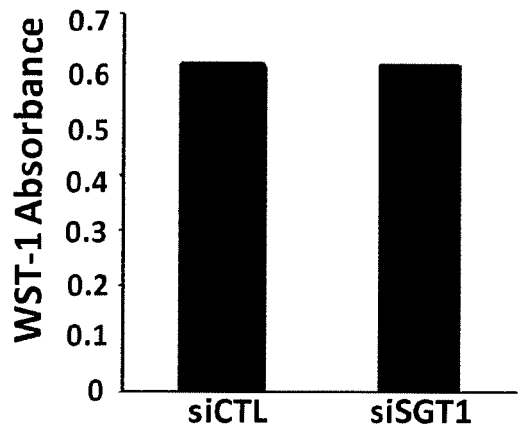
Figure 3B:
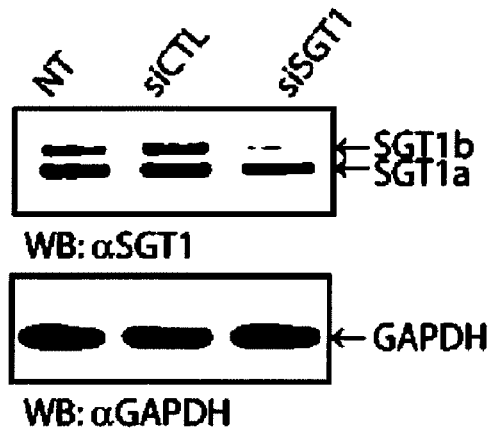
Figure 3B:
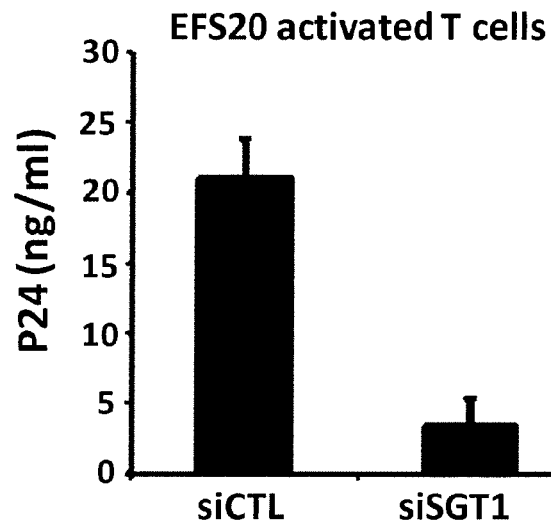
Figure 3B:
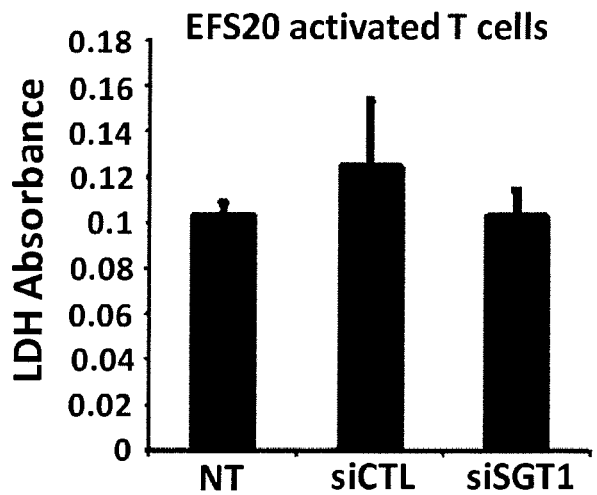
Figure 4A:
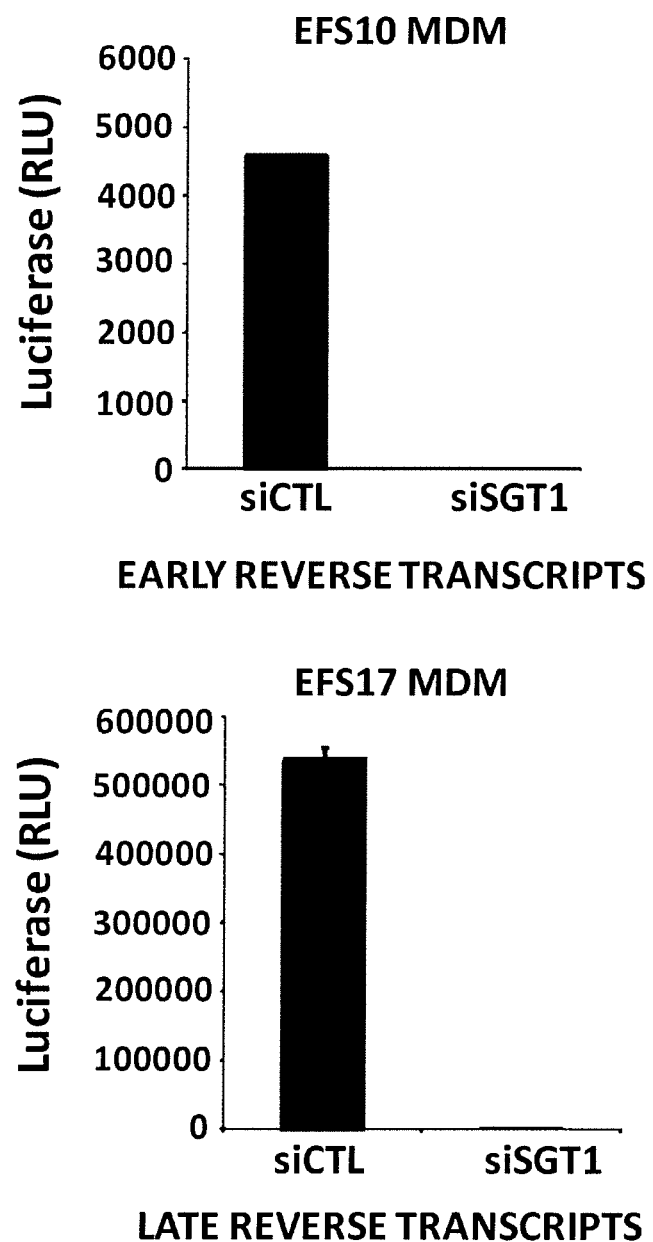
Figure 4B:
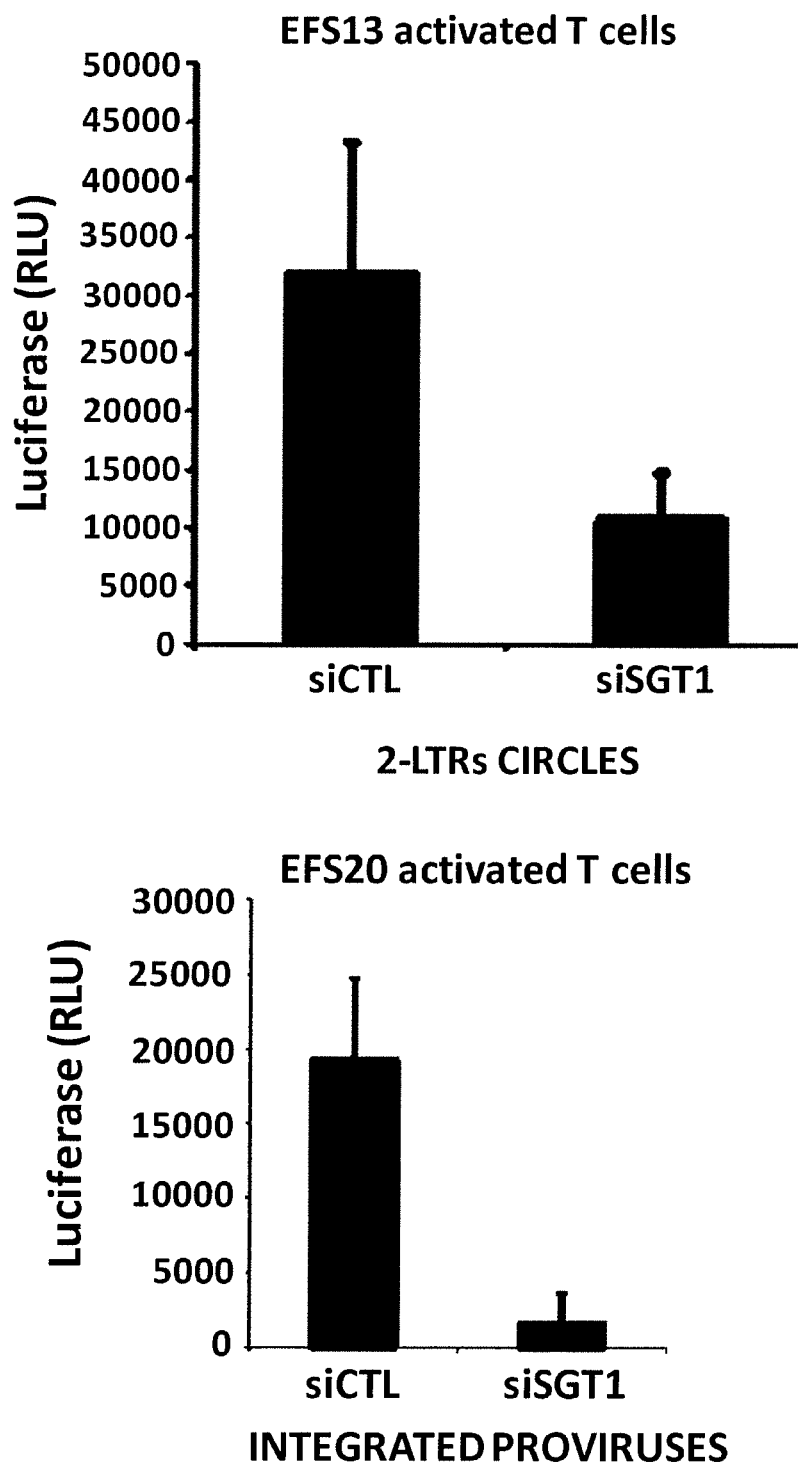
Figure 4C:
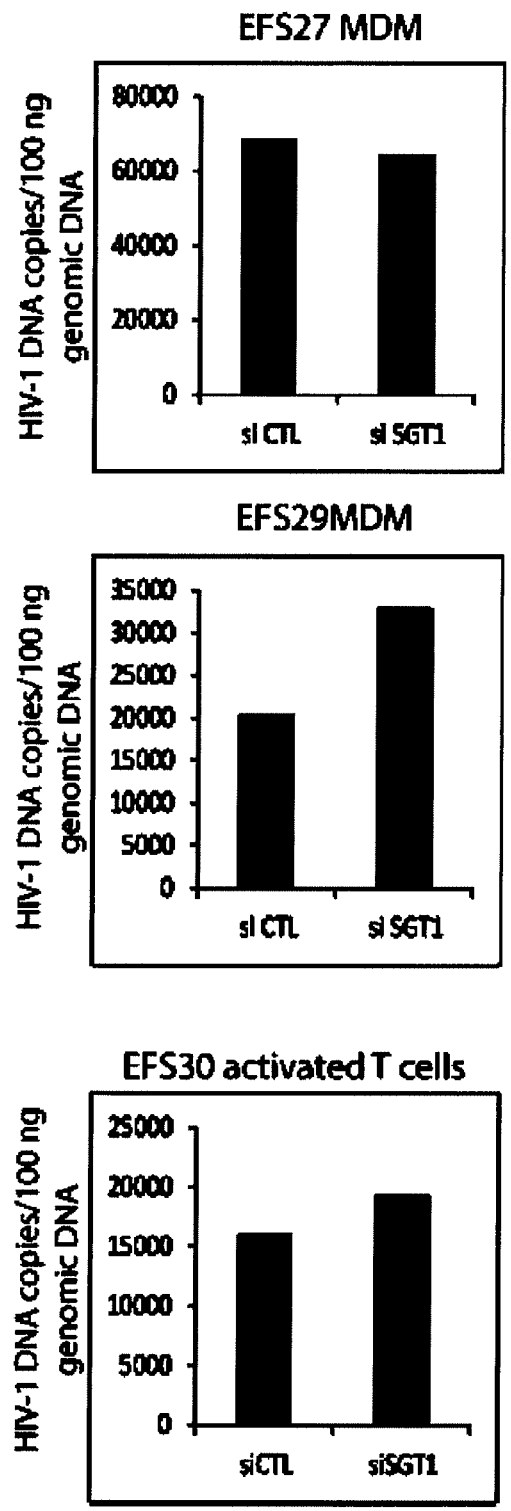
Figure 4D:
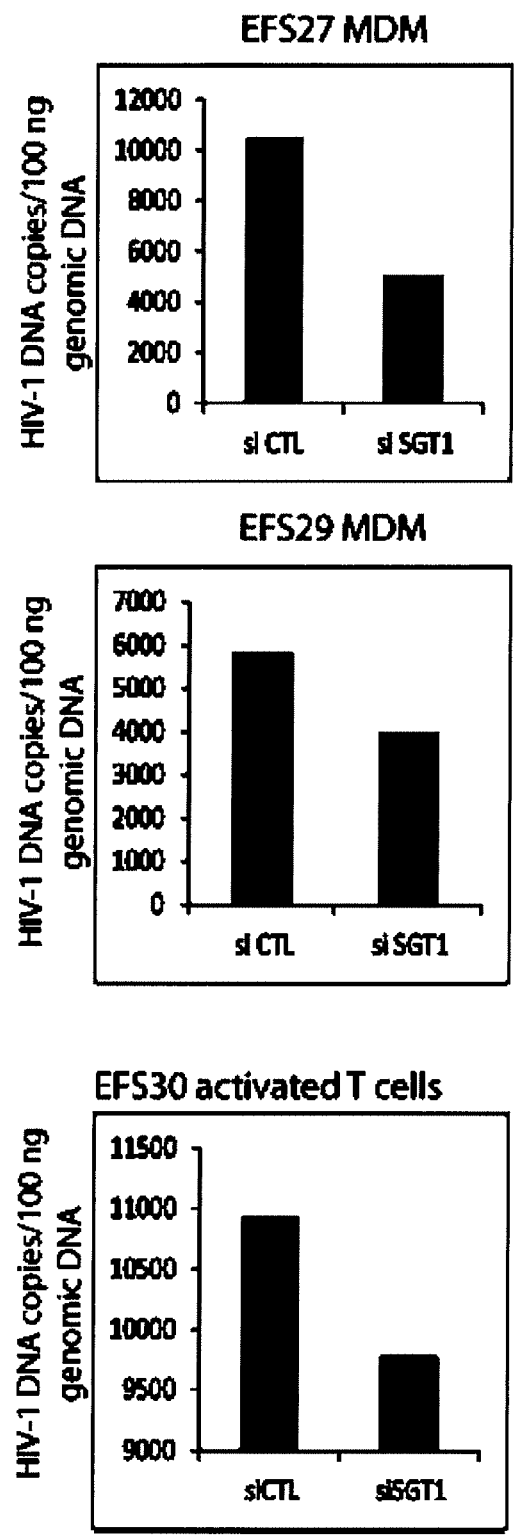
Figure 4E:
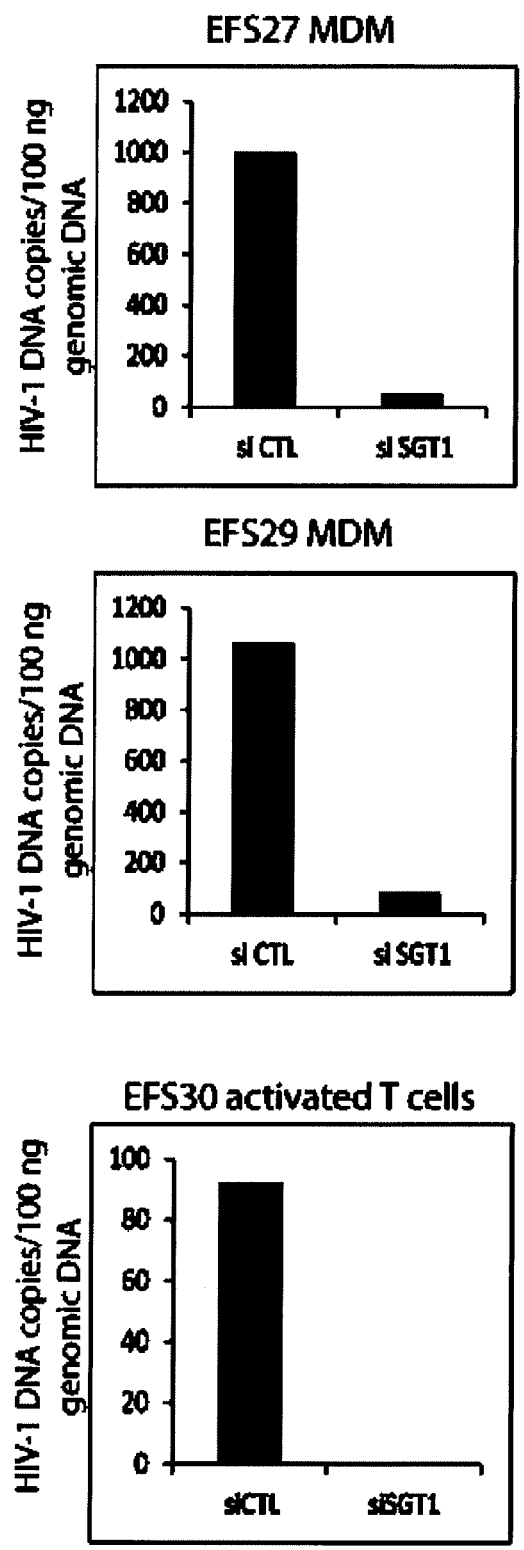
Figure 4F:
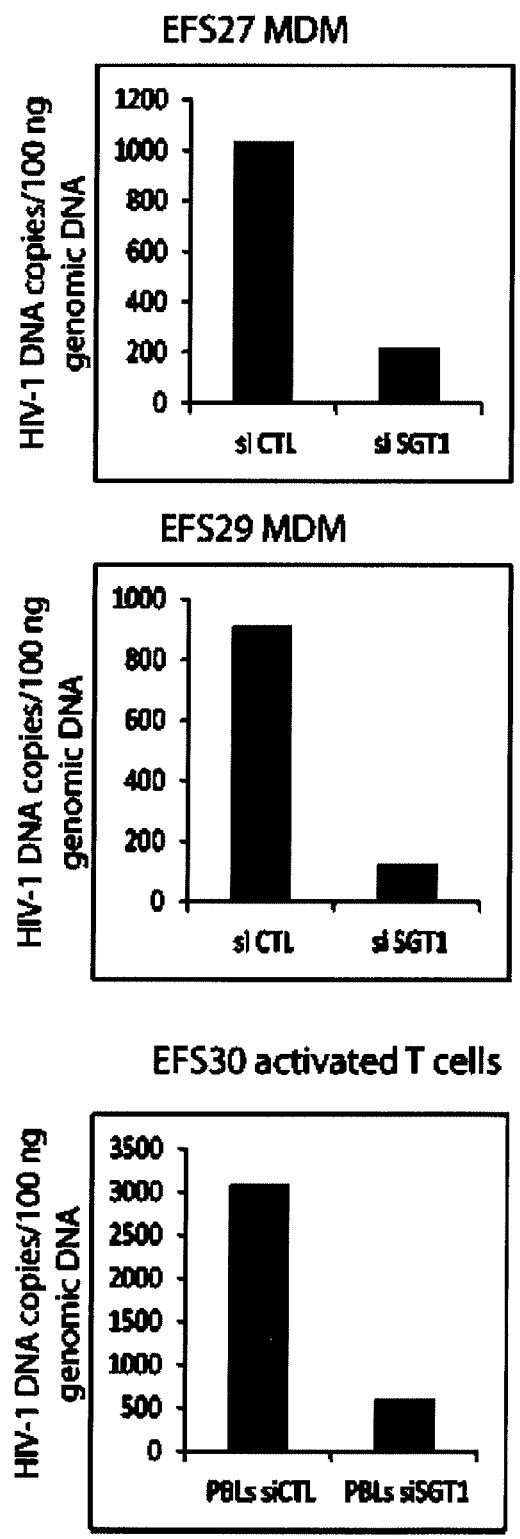

The efficiency of HIV-1 infection was determined by measuring the release of p24CA in the supernatant of macrophages infected during 72 hours. Results reported in FIGS. 2A-C (left panels) showed that with the protocol that we set up for silencing SGT1 in macrophages we obtained an efficient depletion of the protein in three different healthy donors (EFS7, EFS10 and EFS17). Importantly, the silencing of SGT1 in MDM from two donors completely abrogated HIV-1 replication and in one donor (EFS7) (where the SGT1 silencing is less efficient than EFS10 and EFS17) the replication was inhibited by 60% (FIGS. 3A-C middle panels). No cytotoxic effect of SGT1 silencing was detected (using WST1 assay) (FIGS. 3A-C, right panels). These results are representative of additional three different donors. Altogether, these data confirmed previous results and revealed that SGT1 is a crucial cellular protein of HIV-1 replication in macrophages.

We also developed a protocol for silencing SGT1 in activated T Lymphocytes. T cells were obtained from PBMCs of healthy donors of Etablissement Français du Sang (EFS) and then activated by PHA for 24 hours. At five days post-activation, T cells were transfected with smart pool siRNAs targeting SGT1 (siSGT1). Control T lymphocytes were transfected with a pool of non-targeting siRNAs (siCTL). At 72 hours post-siRNAs transfection, activated T cells were infected with NL$_{4.3}$ (X4) Env HIV-1 virus. Viral replication was determined by quantifying CAp24 of the produced HIV-1 in the supernatant of T lymphocytes at 72 hours post-infections. FIG. 2 (A and B top panels) showed that efficient depletion of SGT1 in activated CD4 T cells was obtained from two donors (EFS13 and EFS20) with the set up silencing protocol. Interestingly, the depletion of SGT1 inhibited HIV-1 replication by 95% (FIGS. 3 A and B, middle panels) without affecting cellular proliferation as measured by WST-1 assay (FIG. 3A, bottom panel) and without causing cytotoxicity as measured by lactate dehydrogenase (LDH) activity in the supernatant of transfected T lymphocytes (FIG. 3B, bottom panel). These data are consistent with results obtained in macrophages (FIG. 2) and further indicate that SGT1 is an indispensable cellular protein for HIV-1 replication in the main virus target cells activated T cells and macrophages (for both X4 and R5 viruses).

Silencing effects of SGT1 on HIV-1 infection were unexpected for us because SGT1 was described to be involved in the innate immune response by stabilizing NLR proteins and we hypothesized that by depleting SGT1, HIV-1 infection will be enhanced. However, SGT1 silencing with two different siRNAs in HeLa CD4$^+$CXCR4$^+$ cells and with a pool of 4 different siRNAs in macrophages and activated CD4 T cells inhibited HIV-1 infection without affecting cell viability led us to suggest that SGT1 promotes HIV-1 infection.

SGT1 Promotes HIV-1 Replication at the Early Post-Entry Steps: Reverse Transcription and Nuclear Import.

In order to identify the replication step(s) in which HIV-1 uses SGT1 to perform its replication cycle, we studied the effect of SGT1 depletion in macrophages and in activated T lymphocytes on the different viral steps. To determine whether the viral entry step is involved, SGT1 depleted macrophages and activated T cells infected with R5 and X4 Env HIV-1 viruses, respectively, (results shown in FIGS. 2 and 3) were infected in parallel with HIV-1 strain that is deleted in Env and pseudotyped with VSV-G envelope and expressing luciferase as reporter gene (NL4.3 delta Env-Luc). The data shown in FIGS. 4A and 4B indicate that the siRNA-mediated knockdown of SGT1 in MDM from two donors (EFS 10 and EFS17) and in activated CD4 T cells from two donors (EFS13 and EFS20) strongly inhibited HIV-1 infectivity, as determined by luciferase activity at 72 hours post-infection, of NL4.3 delta Env-Luc (VSV-G) HIV-1 viral strain. This inhibition is at the same extent with that observed with the replication competent HIV-1 viruses (R5 and X4) (FIGS. 2 and 3) and indicates that SGT1 depletion is not affecting viral entry step. These data are representative of five and three additional donors for macrophages and activated T cells, respectively.

To determine whether SGT1 is involved in the viral post-entry steps, we measured by quantitative Real Time PCR (qPCR) the different HIV-1 cDNA species (early and late reverse transcripts, 2-LTR circles and integrated proviruses) in macrophages and activated T cells silenced for SGT1 and infected with NL4.3 delta Env-Luc (VSV-G) HIV-1. As shown in FIGS. 4C, 4D, 4E and 4F, SGT1 silencing does not affect early reverse transcripts (left panels), decreased late reverse transcripts by 50% (middle-left panels) and strongly inhibited 2-LTRs circles (middle-right panels) and integrated proviruses (right panels) by 90% to 100% in macrophages (from two donors, EFS27 and EFS29) and in activated T cells (from one donor, EFS30). The 2-LTRs circles of HIV-1 are formed in the nucleus by the non-homologous-end-joining (NHEJ) recombination of the 5' and 3' LTR DNA ends of the linear viral cDNA that succeed to enter the nucleus but fail to integrate into the human genome. Therefore, the presence of 2-LTRs circles are considered as a hallmark of viral nuclear import and their absence indicate a block at the level of nuclear import.

Datas obtained in FIG. 4 suggested that SGT1 knokdown has a first minor block at the level of the accomplishment of viral reverse transcription followed by a stronger block at the level of nuclear import which consequently abrogates HIV-1 integration. Altogether these results indicate that SGT1 is a cellular factor that promotes early post-entry HIV-1 viral steps. All the SGT1 knockdowns presented in this virological part were controlled for cytotoxcity effects of silencing by WST-1 proliferation assay and for the LDH activity in the supernatant of silenced cells and do not show any cytotoxic effect in the two different cell types: MDM and T lymphocytes.

SGT1 Stabilizes HIV-1 Integrase Expression.

Based on the results obtained in FIG. 4, we hypothesized that SGT1 stabilizes the expression of the viral and cellular proteins that are components of the Reverse Transcription (RTC) and the pre-integration (PIC) complexes and thus promotes the efficient accomplishment of viral cDNA synthesis and nuclear import. We started to test this hypothesis by monitoring the protein expression of the HIV-1 proteins: Nucleocapsid (NC) tagged with hemagglitinin epitope tag (HA), the HA tagged Integrase (HA-IN) and the accessory Viral protein r (Vpr) tagged with the Green Fluorescent Protein (GFP) with simultaneous co-expression of an exogenous human untagged SGT1 (UN-SGT1) in HEK293T cells through transfection of the indicated protein cDNA. Control cells were co-transfected with an untagged GFP (UN-GFP). Interestingly, we observed in three independent experiments that the expression HIV-1 Integrase (HA-IN) was considerably enhanced when SGT1 was over-expressed in HEK293T cells, while the expressions of Nucleocapsid or Vpr were unchanged under these conditions. These data indicate that SGT1 may stabilize the expression of the viral integrase.

CONCLUSION

Our results demonstrated that SGT1 is an indispensable cellular factor that promotes pre-integrative early steps of HIV-1 replication (reverse transcription and nuclear import). In attempt to search molecular mechanisms, we demonstrated that SGT1 stabilizes the expression of the viral integrase (IN), which is one of the important components of HIV-1 pre-integration complex [21, 22]. Interestingly, HIV-1 integrase has been shown to have roles in HIV-1 cDNA synthesis and nuclear import due to its direct interaction with the viral reverse transcriptase and to the cellular factors that are important for the virus nuclear translocation [22, 23].

REFERENCES

Throughout this application, various references describe the state of the art to which this invention pertains. The disclosures of these references are hereby incorporated by reference into the present disclosure.

1. Peterlin, B. M. and D. Trono, *Hide, shield and strike back: how HIV-infected cells avoid immune eradication.* Nat Rev Immunol, 2003. 3(2): p. 97-107.
2. Bergamaschi, A. and G. Pancino, *Host hindrance to HIV-1 replication in monocytes and macrophages.* Retrovirology, 2010. 7: p. 31.
3. Goff, S. P., *Host factors exploited by retroviruses.* Nat Rev Microbiol, 2007. 5(4): p. 253-63.
4. Rasaiyaah, J., et al., *HIV-1 evades innate immune recognition through specific cofactor recruitment.* Nature, 2013. 503(7476): p. 402-5.
5. Yeung, M. L., et al., *A genome-wide short hairpin RNA screening of jurkat T-cells for human proteins contributing to productive HIV-1 replication.* J Biol Chem, 2009. 284(29): p. 19463-73.
6. Zhou, H., et al., *Genome-scale RNAi screen for host factors required for HIV replication.* Cell Host Microbe, 2008. 4(5): p. 495-504.
7. Konig, R., et al., *Global analysis of host-pathogen interactions that regulate early-stage HIV-1 replication.* Cell, 2008. 135(1): p. 49-60.
8. Friedrich, B. M., et al., *Host factors mediating HIV-1 replication.* Virus Res, 2011. 161(2): p. 101-14.
9. Jolly, C., I. Mitar, and Q. J. Sattentau, *Adhesion molecule interactions facilitate human immunodeficiency virus type 1-induced virological synapse formation between T cells.* J Virol, 2007. 81(24): p. 13916-21.
10. Su, B., et al., *Neutralizing antibodies inhibit HIV-1 transfer from primary dendritic cells to autologous CD4 T lymphocytes.* Blood, 2012. 120(18): p. 3708-17.
11. Christ, F. and Z. Debyser, *The LEDGF/p75 integrase interaction, a novel target for anti-HIV therapy.* Virology, 2013. 435(1): p. 102-9.
12. Boter, M., et al., *Structural and functional analysis of SGT1 reveals that its interaction with HSP90 is required for the accumulation of Rx, an R protein involved in plant immunity.* Plant Cell, 2007. 19(11): p. 3791-804.
13. Mayor, A., et al., *A crucial function of SGT1 and HSP90 in inflammasome activity links mammalian and plant innate immune responses.* Nat Immunol, 2007. 8(5): p. 497-503.
14. Kadota, Y., K. Shirasu, and R. Guerois, *NLR sensors meet at the SGT1-HSP90 crossroad.* Trends Biochem Sci, 2010. 35(4): p. 199-207.
15. da Silva Correia, J., et al., *Regulation of Nod1-mediated signaling pathways.* Cell Death Differ, 2007. 14(4): p. 830-9.
16. Schroder, K. and J. Tschopp, *The inflammasomes.* Cell, 2010. 140(6): p. 821-32.
17. Khachatryan, V., et al., *Search for quark compositeness with the dijet centrality ratio in pp collisions at radicals=7 TeV.* Phys Rev Lett, 2010. 105(26): p. 262001.
18. Kitagawa, K., et al., *SGT1 encodes an essential component of the yeast kinetochore assembly pathway and a novel subunit of the SCF ubiquitin ligase complex.* Mol Cell, 1999. 4(1): p. 21-33.
19. Steensgaard, P., et al., *Sgt1 is required for human kinetochore assembly.* EMBO Rep, 2004. 5(6): p. 626-31.
20. Martins, T., et al., *Sgt1, a co-chaperone of Hsp90 stabilizes Polo and is required for centrosome organization.* EMBO J, 2009. 28(3): p. 234-47.
21. Zhan, P., X. Liu, and E. De Clercq, *Blocking nuclear import of pre-integration complex: an emerging anti-HIV-1 drug discovery paradigm.* Curr Med Chem, 2010. 17(6): p. 495-503.
22. Taltynov, O., et al., *Cellular cofactors of lentiviral integrase: from target validation to drug discovery.* Mol Biol Int, 2012. 2012: p. 863405.
23. Chakraborty, A., et al., *Biochemical interactions between HIV-1 integrase and reverse transcriptase.* FEBS Lett, 2013. 587(5): p. 425-9.
24. Zhang, M., et al., *Structural basis for assembly of Hsp90-Sgt1-CHORD protein complexes: implications for chaperoning of NLR innate immunity receptors.* Mol Cell, 2010. 39(2): p. 269-81.
25. Noel, L. D., et al., *Interaction between SGT1 and cytosolic/nuclear HSC70 chaperones regulates Arabidopsis immune responses.* Plant Cell, 2007. 19(12): p. 4061-76.

The invention claimed is:

1. A method for treating HIV-1 infection in a subject in need thereof comprising administering to the subject a therapeutically effective amount of an inhibitor of suppressor of G2 allele of SKP1 (SGT1) activity or expression.

2. The method of claim 1 wherein the inhibitor of SGT1 expression is selected from the group consisting of antisense RNA molecules, antisense DNA molecules, small inhibitory RNAs (siRNAs), short hairpin RNA and ribozymes.

3. The method of claim 1 wherein the inhibitor of SGT1 activity or expression is used in combination with at least one antiretroviral.

4. The method of claim 3 wherein the antiretroviral is selected from the group consisting of nucleoside/nucleotide reverse transcriptase inhibitors, nonnucleoside reverse transcriptase inhibitors (NNRTIs), protease inhibitors (PIs), entry inhibitors, integrase inhibitors, nucleoside reverse transcriptase inhibitors, nucleoside reverse transcriptase inhibitors phosphonate reverse transcriptase inhibitors, compounds of the TIBO (tetrahydro-imidazo[4,5,1-jk][1,4]-benzodiazepine-2(1H)-one and thione)-type compounds of the [alpha]-APA ([alpha]-anilino phenyl acetamide) type inhibitors of trans-activating proteins, protease inhibitors fusion inhibitors, CXCR4 receptor antagonists, inhibitors of a viral integrase; and ribonucleotide reductase inhibitors.

5. The method of claim 4, wherein the NNRTI is efavirenz, etravirine or nevirapine.

6. The method of claim 4, wherein the PI is atazanavir, darunavir or ritonavir.

7. The method of claim 4, wherein the entry inhibitor is enfuvirtide or maraviroc.

8. The method of claim 4, wherein the integrase inhibitor is dolutegravir or raltegravir.

9. The method of claim 3, wherein the antiretroviral is pentamidine, thymopentin, castanospermine, dextran or foscarnet-sodium.

10. The method of claim 4, wherein the nucleoside reverse transcriptase inhibitor is zidovudine, didanosine, zalcitabine, lamivudine, stavudine or abacavir.

11. The method of claim 4, wherein the non-nucleoside reverse transcriptase inhibitor is nevirapine, efavirenz or delavirdine.

12. The method of claim 4, wherein the phosphonate reverse transcriptase inhibitor is tenofovir.

13. The method of claim 4, wherein the compound of the TIBO-type is (S)-8-chloro-4,5,6,7-tetrahydro-5-methyl-6-(3-methyl-2-butenyl)imidazo-[4,5,1-jk][1,4]benzo-diazepine-2(1H)-thione.

14. The method of claim 4, wherein the compound of the [alpha]-APA type is [alpha]-[(2-nitrophenyl)amino]-2,6-dichlorobenzene-acetamide.

15. The method of claim 4, wherein the inhibitor of trans-activating proteins is a TAT-inhibitor.

16. The method of claim 4, wherein the protease inhibitor is indinavir, ritonavir, saquinavir, lopinavir (ABT-378), nelfinavir, amprenavir, TMC-126, BMS-232632, or VX-175.

17. The method of claim 4, wherein the fusion inhibitor is T-20 or T-1249.

18. The method of claim 4, wherein the CXCR4 receptor antagonist is AMD-3100.

19. The method of claim 4, wherein the ribonucleotide reductase inhibitor is hydroxyurea.

\* \* \* \* \*

SEQUENCE LISTING

<160> NUMBER OF SEQ ID NOS: 2

<210> SEQ ID NO 1
<211> LENGTH: 333
<212> TYPE: PRT
<213> ORGANISM: Homo sapiens

<400> SEQUENCE: 1

Met Ala Ala Ala Ala Gly Thr Ala Thr Ser Gln Arg Phe Phe Gln
1               5                   10                  15

Ser Phe Ser Asp Ala Leu Ile Asp Glu Asp Pro Gln Ala Ala Leu Glu
                20                  25                  30

Glu Leu Thr Lys Ala Leu Glu Gln Lys Pro Asp Asp Ala Gln Tyr Tyr
                35                  40                  45

Cys Gln Arg Ala Tyr Cys His Ile Leu Leu Gly Asn Tyr Cys Val Ala
            50                  55                  60

Val Ala Asp Ala Lys Lys Ser Leu Glu Leu Asn Pro Asn Asn Ser Thr
65                  70                  75                  80

Ala Met Leu Arg Lys Gly Ile Cys Glu Tyr His Glu Lys Asn Tyr Ala
                85                  90                  95

Ala Ala Leu Glu Thr Phe Thr Glu Gly Gln Lys Leu Asp Ser Ala Asp
                100                 105                 110

Ala Asn Phe Ser Val Trp Ile Lys Arg Cys Gln Glu Ala Gln Asn Gly
                115                 120                 125

Ser Glu Ser Glu Val Trp Thr His Gln Ser Lys Ile Lys Tyr Asp Trp
            130                 135                 140

Tyr Gln Thr Glu Ser Gln Val Val Ile Thr Leu Met Ile Lys Asn Val
145                 150                 155                 160

Gln Lys Asn Asp Val Asn Val Glu Phe Ser Glu Lys Glu Leu Ser Ala
                165                 170                 175

Leu Val Lys Leu Pro Ser Gly Glu Asp Tyr Asn Leu Lys Leu Glu Leu
                180                 185                 190

Leu His Pro Ile Ile Pro Glu Gln Ser Thr Phe Lys Val Leu Ser Thr
            195                 200                 205

Lys Ile Glu Ile Lys Leu Lys Lys Pro Glu Ala Val Arg Trp Glu Lys
210                 215                 220

Leu Glu Gly Gln Gly Asp Val Pro Thr Pro Lys Gln Phe Val Ala Asp
225                 230                 235                 240

Val Lys Asn Leu Tyr Pro Ser Ser Ser Pro Tyr Thr Arg Asn Trp Asp
                245                 250                 255

Lys Leu Val Gly Glu Ile Lys Glu Glu Lys Asn Glu Lys Leu Glu
            260                 265                 270

Gly Asp Ala Ala Leu Asn Arg Leu Phe Gln Gln Ile Tyr Ser Asp Gly
            275                 280                 285

Ser Asp Glu Val Lys Arg Ala Met Asn Lys Ser Phe Met Glu Ser Gly
                290                 295                 300

Gly Thr Val Leu Ser Thr Asn Trp Ser Asp Val Gly Lys Arg Lys Val
305                 310                 315                 320

Glu Ile Asn Pro Pro Asp Asp Met Glu Trp Lys Lys Tyr
                325                 330

<210> SEQ ID NO 2
<211> LENGTH: 365
<212> TYPE: PRT
<213> ORGANISM: Homo sapiens -continued

<400> SEQUENCE: 2

```
Met Ala Ala Ala Ala Gly Thr Ala Thr Ser Gln Arg Phe Phe Gln
1               5                   10                  15

Ser Phe Ser Asp Ala Leu Ile Asp Glu Asp Pro Gln Ala Ala Leu Glu
            20                  25                  30

Glu Leu Thr Lys Ala Leu Glu Gln Lys Pro Asp Asp Ala Gln Tyr Tyr
            35                  40                  45

Cys Gln Arg Ala Tyr Cys His Ile Leu Leu Gly Asn Tyr Cys Val Ala
    50                  55                  60

Val Ala Asp Ala Lys Lys Ser Leu Glu Leu Asn Pro Asn Asn Ser Thr
65                  70                  75                  80

Ala Met Leu Arg Lys Gly Ile Cys Glu Tyr His Glu Lys Asn Tyr Ala
                85                  90                  95

Ala Ala Leu Glu Thr Phe Thr Glu Gly Gln Lys Leu Asp Ile Glu Thr
            100                 105                 110

Gly Phe His Arg Val Gly Gln Ala Gly Leu Gln Leu Leu Thr Ser Ser
        115                 120                 125

Asp Pro Pro Ala Leu Asp Ser Gln Ser Ala Gly Ile Thr Gly Ala Asp
    130                 135                 140

Ala Asn Phe Ser Val Trp Ile Lys Arg Cys Gln Glu Ala Gln Asn Gly
145                 150                 155                 160

Ser Glu Ser Glu Val Trp Thr His Gln Ser Lys Ile Lys Tyr Asp Trp
                165                 170                 175

Tyr Gln Thr Glu Ser Gln Val Val Ile Thr Leu Met Ile Lys Asn Val
            180                 185                 190

Gln Lys Asn Asp Val Asn Val Glu Phe Ser Glu Lys Glu Leu Ser Ala
        195                 200                 205

Leu Val Lys Leu Pro Ser Gly Glu Asp Tyr Asn Leu Lys Leu Glu Leu
    210                 215                 220

Leu His Pro Ile Ile Pro Glu Gln Ser Thr Phe Lys Val Leu Ser Thr
225                 230                 235                 240

Lys Ile Glu Ile Lys Leu Lys Lys Pro Glu Ala Val Arg Trp Glu Lys
                245                 250                 255

Leu Glu Gly Gln Gly Asp Val Pro Thr Pro Lys Gln Phe Val Ala Asp
            260                 265                 270

Val Lys Asn Leu Tyr Pro Ser Ser Ser Pro Tyr Thr Arg Asn Trp Asp
        275                 280                 285

Lys Leu Val Gly Glu Ile Lys Glu Glu Glu Lys Asn Glu Lys Leu Glu
    290                 295                 300

Gly Asp Ala Ala Leu Asn Arg Leu Phe Gln Gln Ile Tyr Ser Asp Gly
305                 310                 315                 320

Ser Asp Glu Val Lys Arg Ala Met Asn Lys Ser Phe Met Glu Ser Gly
                325                 330                 335

Gly Thr Val Leu Ser Thr Asn Trp Ser Asp Val Gly Lys Arg Lys Val
            340                 345                 350

Glu Ile Asn Pro Pro Asp Asp Met Glu Trp Lys Lys Tyr
        355                 360                 365
```